United States Patent
Kopotic et al.

(10) Patent No.: US 6,470,199 B1
(45) Date of Patent: Oct. 22, 2002

(54) ELASTIC SOCK FOR POSITIONING AN OPTICAL PROBE

(75) Inventors: Robert J. Kopotic, Jamul; Gene Mason, La Mirada, both of CA (US)

(73) Assignee: Masimo Corporation, Irvine, CA (US)

( * ) Notice: Subject to any disclaimer, the term of this patent is extended or adjusted under 35 U.S.C. 154(b) by 14 days.

(21) Appl. No.: 09/598,930

(22) Filed: Jun. 21, 2000

(51) Int. Cl.$^7$ .................................................. A61B 5/00
(52) U.S. Cl. ........................ 600/344; 600/310; 600/323
(58) Field of Search ................................ 600/309–310, 600/322–326, 344

(56) References Cited

U.S. PATENT DOCUMENTS

| | | | | |
|---|---|---|---|---|
| 4,907,594 | A | * 3/1990 | Muz | 600/335 |
| 5,159,929 | A | * 11/1992 | Morris et al. | 600/411 |
| 5,776,059 | A | * 7/1998 | Kaestle et al. | 600/340 |
| 5,782,757 | A | 7/1998 | Diab et al. | |
| 5,842,982 | A | 12/1998 | Mannheimer | |
| 6,016,575 | A | 1/2000 | Prychak | |
| 6,047,201 | A | * 4/2000 | Jackson, III | 600/344 |
| 6,179,159 | B1 | * 1/2001 | Gurley | 221/26 |
| 6,224,548 | B1 | * 5/2001 | Gopinathan et al. | 600/300 |
| 6,292,686 | B1 | * 9/2001 | Chaiken et al. | 600/476 |

OTHER PUBLICATIONS

Surgilast, "*Tubular Elastic Dressing Retainer and Pre–Cut Tubular Elastic Retainers Dressing*", 9 pages.

Apgar, M.D., Virginia, "*A Proposal for a New Method of Evaluation of the Newborn Infant*", (Jul.–Aug. 1953), pp. 260–267.

Gilbert, C., et al., "*Retinopathy of Prematurity in Middle–Income Countries*", The Lancet, vol. 350, (Jul. 5, 1997), pp. 12–14.

Reddy, M.D., et al., "*Pulse Oximetry Saturations in the First 6 Hours of Life in Normal Infants*", Clinical Pediatrics, (Feb. 1999), pp. 87–92.

Softees Medicated Skin Protectors Advertisement, Med–Design Company, 3 pages.

* cited by examiner

*Primary Examiner*—Eric F. Winakur
*Assistant Examiner*—Matthew J Kremer
(74) *Attorney, Agent, or Firm*—Knobbe, Martens, Olson & Bear, LLP

(57) ABSTRACT

A positioner, such as an elastic sock, is fitted with an optical probe, preferably designed for pulse oximetry. The sock preferably substantially forms to the shape of a wearer's foot or hand. In addition, the sock preferably comprises at least one positioning portion. According to one embodiment, the positioning portion is configured to receive at least a wearer's great toe, thumb, or finger, such that the sock maintains substantially opposing alignment of an emitter and a detector. Alternatively, the positioner may comprise a toecap, a glove, or a mitten. The positioner may also advantageously be fitted with a timer circuit, preferably providing an alarm at predetermined intervals.

59 Claims, 4 Drawing Sheets

ELASTIC SOCK FOR POSITIONING AN OPTICAL PROBE

BACKGROUND OF THE INVENTION

1. Field of the Invention

The present invention relates in general to the use of optical probes, and relates in particular to an elastic sock for containing and positioning a pulse oximetry probe.

2. Description of the Related Art

An optical probe generally operates by measuring a light signal passed through a medium. In oximetry, the optical probe attaches to an oximeter system such that the oximeter system determines at least one characteristic of the medium. In the medical field, a pulse oximetry probe measures a light signal passed through tissue. The light signal varies depending on, among other things, the oxygen saturation of the blood cells in the tissue. The oximeter system processes the measured light signals from the pulse oximetry probe and can determine characteristics of the tissue, including a pulse rate and blood oxygen saturation. The pulse oximetry probe is typically placed on an extremity, such as a finger, toe, hand, or foot of the person being monitored.

Today, pulse oximetry is a widely accepted and successful non-invasive technique for monitoring characteristics of patients. In addition, the conventional pulse oximeter probe is manufactured in a wide number of shapes and sizes. Generally, each shape and size typically employs adhesion-based, spring-tension-based, or hook-and-loop-based securing mechanisms to position and secure the optical probe to a measurement site.

However, the foregoing conventional securing mechanisms are often unworkable in certain environments. For example, adhesive-based securing mechanisms simply to not adhere to surfaces that are wet and/or fluid-covered, such as infant skin immediately following birth. For example, in the baby born at or near term, skin coatings such as vernix present adhesion problems, and in the preterm infant, adhesive-based sensors can harm the infant's fragile skin. There are similar problems with the use of adhesive-based sensors during the treatment of burn victims.

Moreover, hook-and-loop-based securing mechanisms, such as Velcro straps, are often applied incorrectly. For example, the Velcro strap may be so loose that the optical probe falls off or that the optical probe emitter becomes misaligned from the optical probe detector during clinician-imposed or self agitation. On the other hand, the Velcro strap may be so tight that they may cause poor perfusion and sores. The foregoing drawbacks are especially apparent with newborns.

In addition to the forgoing infant concerns, environments including severely damaged and/or sensitive tissue, such as burns or the like, pose a number of problems for the conventional securing mechanisms. For example, adhesive-based securing mechanisms may affix itself to fragile newly healed skin such that removal of the adhesive causes the skin to tear, thereby redamaging the tissue and causing pain to the patient. Moreover, the Velcro-based securing mechanisms may again apply too little or too much pressure. Spring-tension-based or pressure-based securing mechanisms, such as a clothespin-type clip mechanism, do not allow the skin to breathe, can restrict blood flow and are only recommended for short-term application.

Velcro-based securing mechanisms suffer from the additional drawback that they need a multistep positioning and securing process in order to apply the optical probe to a measurement site. First, the optical probe is placed on the measurement site and then the Velcro strap is secured. In highly agitated environments, such as those associated with newborns, patient transport, exercise testing and ICU care, a multistep process is burdensome and often difficult for the clinician.

Although conventional securing mechanisms are often unworkable in the foregoing environments, the need for non-invasive monitoring in those environments remains. For example, medical practitioners routinely use the Apgar Score to intermittently assess the well being of newborns just after delivery. Two of the typical five components of the Apgar Score, the heart or pulse rate, and degree of oxygenation, e.g., skin color, can readily and accurately be measured continuously using pulse oximetry. In fact, pulse oximetry provides a much more precise monitoring of these foregoing components. For example, pulse oximetry provides a continuous display of the parameters being measured as opposed to the typical Apgar parameters involving clinician auscultation of the chest for a heart rate or the clinician assessment of the coloration of the skin for the blood oxygen saturation.

Based on the foregoing, a need exists for a securing mechanism capable of functioning in environments hostile to adhesive-based, spring-tension-based, and/or hook-and-loop-based securing mechanisms.

SUMMARY OF THE INVENTION

Accordingly, one aspect of the instant invention is to provide a securing mechanism for an optical probe capable of functioning in a wide variety of potential environments, including those which are hostile to adhesive-based, spring-tension-based, and/or hook-and-loop-based securing mechanisms. The securing mechanism preferably comprises an elastic sock fitted with an optical probe. According to one embodiment, the sock preferably conforms to a wearer's foot and comprises at least one toe portion. The at least one toe portion is preferably positioned around the wearer's great toe or toes, such that the sock maintains a substantially opposing alignment of an emitter and a detector of the optical probe.

According to another embodiment, the sock preferably conforms to a wearer's hand and comprises at least one finger portion. The at least one finger portion is preferably positioned around one or more of the wearer's three middle fingers, such that the sock maintains a substantially opposing alignment of an emitter and a detector of the optical probe.

According to another aspect of the invention, the sock may also advantageously be fitted with a manually activated timer circuit, preferably providing an alarm at predetermined intervals, such as those intervals associated with sequencing Apgar scoring.

Therefore, one aspect of the invention includes an optical probe positioner comprising a sock fitted with an optical probe wherein the optical probe measures at least one characteristic of tissue at a measurement site. In addition, the sock comprises an elastomeric material such that the sock substantially conforms to a wearer's foot or hand, thereby forming a friction fit over a large surface area.

According to another aspect, the invention includes a method of securing an optical probe to tissue at a measurement site in order to determine a characteristic of the tissue. The method comprises propositioning components of an optical probe in a sock such that single motion application of the sock to a measurement site is accomplished by pulling the sock over tissue at the measurement site. In addition, the measurement site is located on a wearer's foot, toes, hand, finger, or thumb.

BRIEF DESCRIPTION OF THE DRAWINGS

The present invention is described in more detail below in connection with the attached drawings, which are meant to illustrate and not limit the invention, and in which.

DETAILED DESCRIPTION OF THE PREFERRED EMBODIMENT

The inventions are described in detail below with reference to the figures, wherein like elements are referenced with like numerals throughout.

Figure 1:
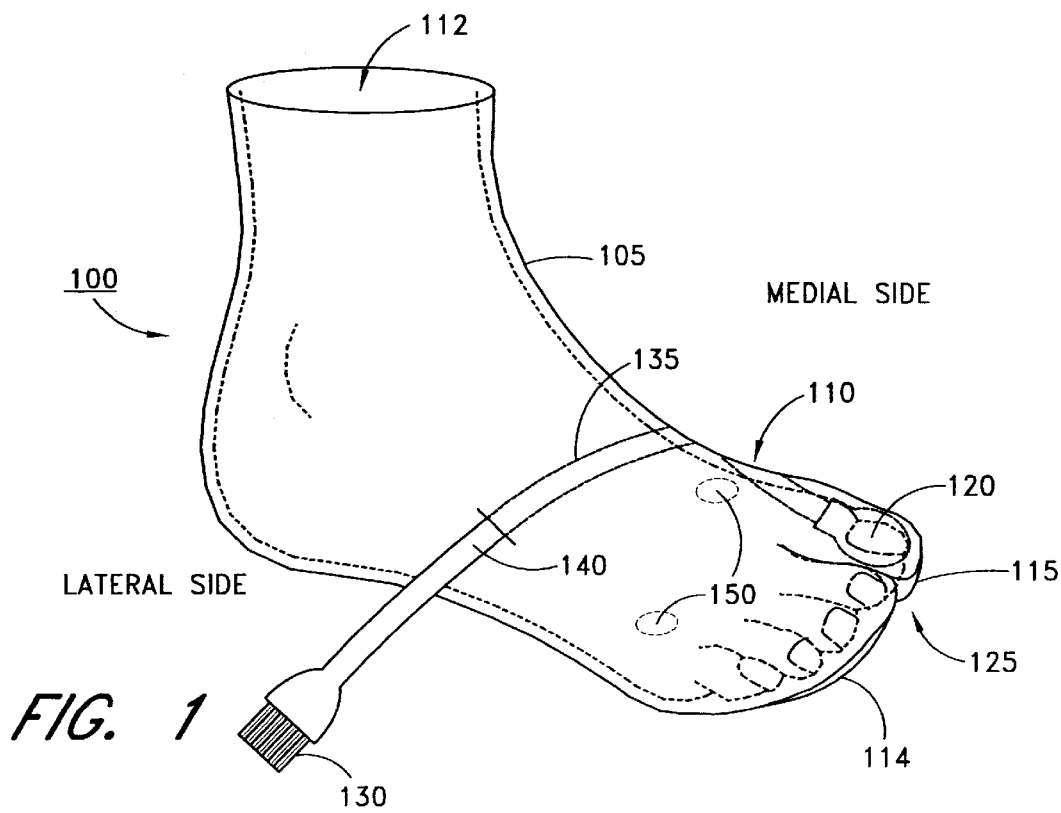
FIG. 1 illustrates a perspective view of a probe positioner having features according to an embodiment of the invention.

FIG. 1 illustrates a perspective view of a probe positioner 100 having features according to an embodiment of the invention. As shown in FIG. 1, the probe positioner 100 includes a sock 105 fitted with an optical probe 110. The sock 105 is configured to receive the foot of a wearer so as to position and substantially secure the optical probe 110 over a measurement site. The optical probe 110 preferably measures at least one light signal passed through tissue at the measurement site. The optical probe 110 communicates via a connector 130 with a monitoring device (not shown), such as an oximeter system, to process the measured light signal in order to determine at least one characteristic of the tissue. For example, the oximeter system preferably determines the wearer's pulse rate, blood oxygen saturation, or both, at the measurement site.

By substantially securing the optical probe 110 to a measurement site, the sock 105 advantageously obviates the need for an adhesive-based, spring-tension-based, or a hook-and-loop-based securing mechanism. Moreover, the sock 105 is advantageously suited for the problematic environments having fluids and/or sensitive skin issues. In addition, the sock 105 preferably provides single step placement of the optical probe 110, in that the sock 105 preferably slips over the wearer's foot and positions the optical probe 110, all in the motion applying the sock to the foot.

As shown in FIG. 1, the preferred embodiment of the sock 105 includes an upper section having an opening 112 configured to receive the foot of the wearer. The sock 105 also includes a lower section having a closure 114 such that the toes of the foot preferably abut the closure 114 of the sock 105. The sock 105 preferably comprises an elastomeric material, such as a stretchable fiber and/or weave. The elastomeric material preferably stretches during application of the sock 105 to the wearer's foot, and shrinks thereafter, such that the sock 105 substantially forms to the shape of the wearer's foot. Preferably, the sock 105 is configured for various foot sizes such that the elasticity of the material applies only a small amount of pressure to the tissue of the measurement site. Thus, the preferred embodiment of the sock 105 provides a securing mechanism that substantially forms to the shape of the wearer's foot, thereby providing positioning rigidity over a wide surface area. Accordingly, the sock 105 advantageously avoids the application of pressure sufficient to cause poor circulation and/or sores on a small surface area.

According to another embodiment the sock 105 comprises material that helps isolate the optical probe 110 from ambient light, thereby improving the signal-to-noise ratio. For example, the material may include black plastic films, such as, for example, those commercially available from E.I. du Pont de Nemours and Company. The material may include metal foils or thick foams, such as, for example, those commercially available from 3M, or the material may include metallized plastic films, such as, for example, those commercially available from Astral Technologies.

According to a preferred embodiment, the sock 105 and optical probe 110 need not be sterile. On the other hand, according to an alternative embodiment, the sock 105 and the optical probe 110 may advantageously be sterile, or sterilized, for use in some medical environments. For example, the sock 105 and optical probe 110 may be sterile for environments having open wounds or exposed tissue, such as, for example, burn victim environments. However, according to the preferred embodiment, sterilization is typically not necessary.

The sock 105 is preferably disposable. For example, when the sock 105 form fits to the wearer's foot in environments involving fluids and/or sensitive tissue, the sock 105 will likely become soiled. In the case of just-delivered newborns, fluids and a slick substance called vernix covers the skin. These fluids and vernix are often already contaminated. Thus, disposing of the sock 105 advantageously avoids cross-patient contamination.

Although the foregoing has disclosed the sock 105 in terms of preferred and alternative embodiments, a skilled artisan will recognize from the disclosure herein a wide number of advantageous materials, shapes, sizes, and manners of operation. For example, the sock 105 may comprise reinforced elastic sections for greater securement near, for example, the opening 112 of the upper section. Moreover, the sock 105 may comprise a tubular stretch net, such as that commercially available under the trade name Surgilast® Elastic Net Dressings. These tubular stretch net materials are conventionally used for securing bandages on burn victims and can be adapted for use on virtually any portion of the body. According to an alternative embodiment, the foregoing tubular stretch nets may be initially sterile or sterilized for use in medical environments where sterilization is preferred.

FIG. 1 also illustrates the sock 105 including a positioning portion 115. The positioning portion 115 configures the closure 114 of the lower section of the sock 105 such that it separately receives the great toe of the wearer's foot. The positioning portion 115 preferably comprises a pocket-like structure similar to that of the finger of a glove. The positioning portion 115 advantageously prevents rotation of the sock 105 around the wearer's foot, thereby advantageously providing additional securement for the optical probe 110.

According to the preferred embodiment, the optical probe 110 includes an emitter 120 and a detector 125. The optical probe 110 preferably communicates with the oximeter system (not shown) through the connector 130 and a flex circuit 135. The flex circuit 135 preferably connects the connector 130 to the emitter 120 and the detector 125 such that the appropriate electrical drive and detection signals are communicated to and from the oximeter system. According to the preferred embodiment, the flex circuit 135 includes a first and second section. Preferably, the first section is partially incorporated into the material of the sock 105, and the second section protrudes through an opening 140 in the sock 105 on either the dorsal or lateral side of the wearer's foot. The second section preferably connects to the connector 130. As shown in FIG. 1, the incorporation of at least part of the flex circuit 135 into the material of the sock 105 advantageously positions the connector 130 away from the wearer, thereby positioning the connector 130 to be conveniently accessible for connection with the oximeter system.

According to the preferred embodiment, the first section of the flex circuit 135 is Y-shaped (as further illustrated in FIG. 2) such that each branch of the "Y" connects one of the emitter 120 and the detector 125. The Y-shape of the preferred flex circuit 135 advantageously allows for variations in the distance between the emitter 120 and the detector 125. Moreover, according to the preferred embodiment, the optical probe 110 accounts for motion artifacts caused by caregiver or wearer agitation. U.S. Pat. No. 5,782,757, issued on Jul. 21, 1998 to Diab, et al., discloses a neonatal optical probe having a Y-shaped flex circuit, and is incorporated herein by reference.

Although the probe positioner 100 is described according to its preferred embodiment having the Y-shaped flex circuit 135, a skilled artisan will recognize a wide number of connection mechanisms for electrically connecting the emitter 120 and the detector 125 to the connector 130. For example, the emitter 120 and the detector 125 may advantageously be electrically connected through wires incorporated into the sock 105. Such wires may include portions bundled or grouped together, and may follow a number of paths or patterns through the sock 105.

FIG. 1 also illustrates the emitter 120 and the detector 125 of the optical probe 110 preferably contacting the surface of the tissue at the measurement site. According to the preferred embodiment, the emitter 120 contacts the nail portion of the great toe, while the detector 125 contacts the skin of the great toe substantially opposite from the nail portion. A skilled artisan will recognize from the disclosure herein that a wide number of shapes of the optical probe 110, along with a wide number of measurement sites, may be chosen based to some degree on the relationship between the optical probe 110 and the measurement site. For example, a reflective probe may advantageously be mounted in a head cap rather than mounted in the preferred sock 105. Moreover, the optical probe 110 may be mounted in a glove, a mitten, a slipper, or virtually any type of suitable garment. Preferably, such garments are advantageously workable in patient treatment environments.

Use of the positioning portion 115 to align the emitter 120 substantially opposite the detector 125 allows for the prepositioning of the optical probe 110 within the sock 105. This prepositioning of the optical probe 110 advantageously enables single motion application of the sock to the wearer even in highly agitated environments.

Although the foregoing has disclosed the positioning portion 115 in terms of preferred and alternative embodiments, a skilled artisan will recognize from the disclosure herein a wide number of modifications available to increase the securement of the sock 105 to the wearer. For example, some or all of the other toes may have corresponding toe portions. On the other hand, the positioning portion 115 may include a flexible clip for positioning the emitter 120 substantially opposite the detector 125. The flexible clip may advantageously be secured between the great and adjoining toe, between multiple toes, or partially or wholly circumscribe the great or adjoining toe. The flexible clip may advantageously be incorporated into the material of the sock 105 and/or comprise reinforced or otherwise more rigid material.

The foregoing probe positioner 100 is advantageously suited for monitoring newly delivered infants. As discussed in the foregoing, the use of the probe positioner 100 in such an environment allows for continuous and increased accuracy in Apgar scoring. Accordingly, one embodiment of the invention preferably includes a timer. The timer is preferably incorporated into the oximeter system circuitry such that an alarm assists clinicians in sequencing the Apgar scoring. For example, the oximeter system may advantageously include an actuator that activates timing functions. The timer preferably activates the alarm at one minute, five minutes, and/or ten minutes after actuation, thereby indicating to a clinician that the Apgar score should be taken. Although the timer is disclosed according to a preferred embodiment, a skilled artisan will recognize from the disclosure herein a wide number of timing implementations and uses. For example, each actuation of the actuator may activate the timer to a predefined time limit. Moreover, the alarm may advantageously include an audio and/or visual alarm on the oximeter system or the probe positioner 100. According to another embodiment, the probe positioner 100 comprises a timer having a timer circuit, an alarm indicator and actuator. The depression of the actuator activates the timer circuit, and, after a predetermined amount of time, the timer circuit activates the alarm indicator. According to yet another embodiment, the optical probe 110 includes a timer circuit. In this embodiment, the timer circuit preferably comprises a counter for counting the drive signals pulsed to the emitter 120. After a predetermined amount of pulses, the timer circuit activates the alarm indicator. Although disclosed as preferred and alternative embodiments, a skilled artisan will recognize that features of the foregoing timers may be advantageously shared and/or incorporated into any of the embodiments disclosed herein.

Although the probe positioner 100 is disclosed according to the preferred and alternative embodiments of positioning the optical probe 110 over one of the wearer's toes, a skilled artisan will recognize from the disclosure herein other measurement sites that may advantageously be used. For example, FIG. 1 illustrates other measurement sites 150 for preferably positioning the emitter 120 of the optical probe 110. Such alternative sites 150 may be advantageous for patients having poor perfusion in the furthest extremities, such as, for example, elderly individuals generally having reduced perfusion in their toes.

Figure 2:
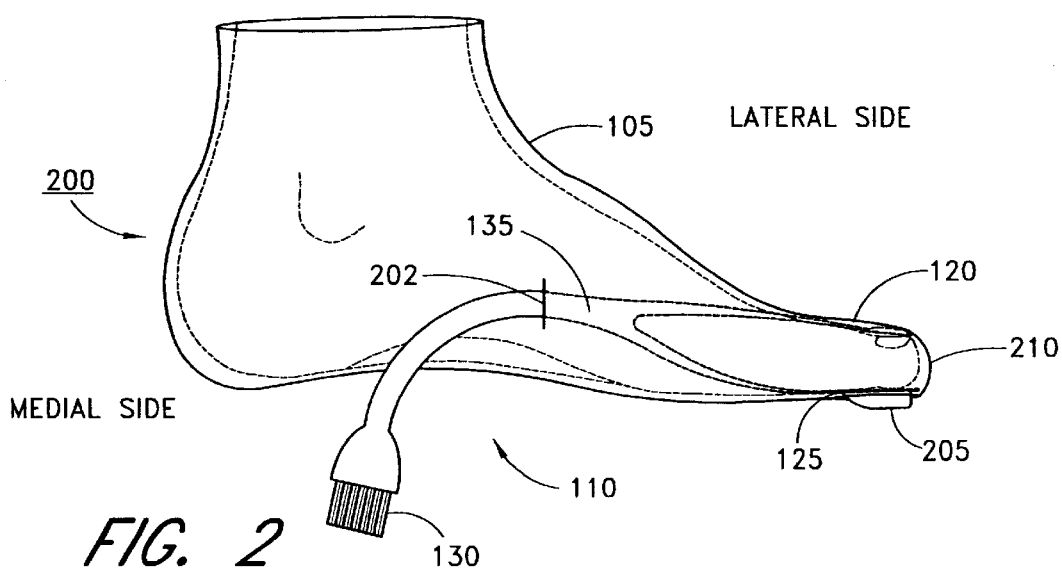
FIG. 2 illustrates a side view of a probe positioner having features according to another embodiment of the invention.

FIG. 2 illustrates a side view of a probe positioner 200 having features according to another embodiment of the invention. As shown in FIG. 2, the sock 105 is fitted with the optical probe 110 on the medial side of the wearer's foot. According to this embodiment, the second portion of the flex circuit 135 extends from an opening 202 on the medial side of the sock 105. Moreover, the perspective of FIG. 2 illustrates the placement of the emitter 120 and the detector 125 relative to the great toe. According to this embodiment, the detector 125 includes an extending portion 205 protruding through an opening 210 in the sock 105. The opening 210 is preferably through the outside of the sock 105 such that the sock 105 does not stretch around the extending portion 205. The opening 210 advantageously provides a closer and more even form fit to the grand toe, thereby providing additional securement of the optical probe 110.

Figure 3A:
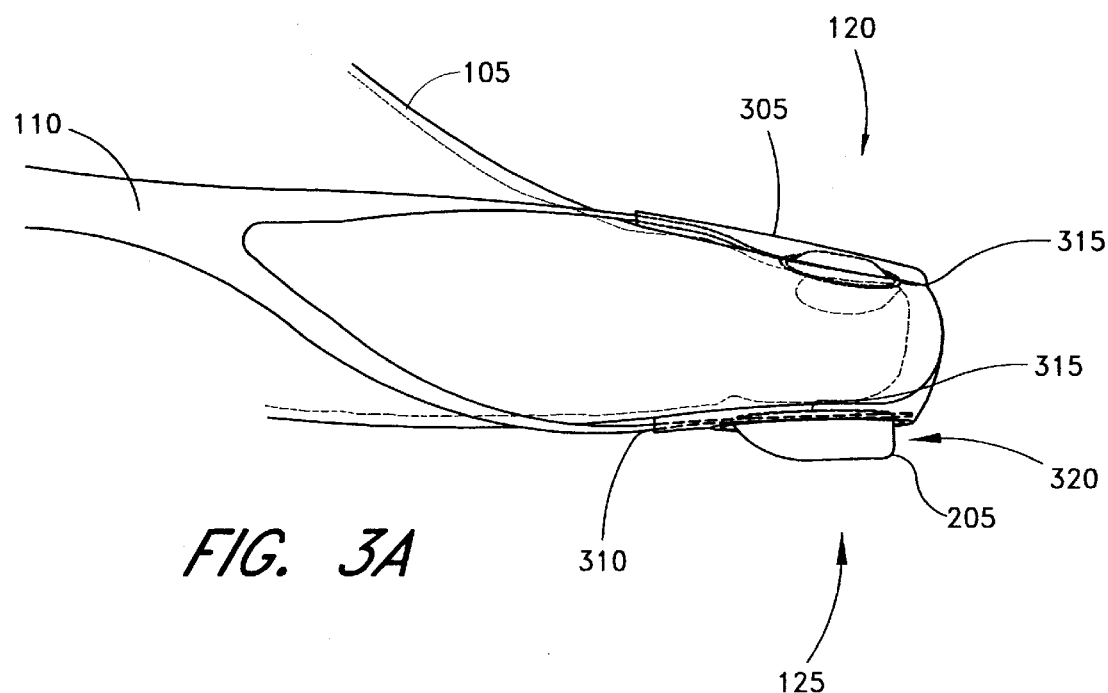
FIG. 3A illustrates a side view of a probe positioner having features according to yet another embodiment of the invention.

FIG. 3A illustrates a side view of a probe positioner 300 having features according to yet another embodiment of the invention. According to this embodiment, the sock 105 remains disposable, while the circuitry of the optical probe 110 is generally reusable. Reusable circuitry advantageously reduces the cost per probe positioner 300. According to this embodiment, the probe positioner 300 includes an emitter pocket 305 and a detector pocket 310 for inserting the optical probe 110 into the sock 105. The material of the pockets 305 and 310 preferably includes elastomeric or otherwise reinforced material. Thus, when the emitter 120 is inserted into the emitter pocket 305, and the detector 125 is inserted into the detector pocket 310, the friction fit of the pockets 305 and 310, preferably and secures the optical probe 110 to a measurement site.

Also as shown in FIG. 3A, the pockets 305 and 310 preferably include tissue-side openings 315. The tissue-side openings 315 are preferably sized and constructed so as to allow the emitter 120 and the detector 125 to contact, and be secured against, the tissue of the great toe. According to another embodiment, the detector pocket 310 preferably includes an ambient-side opening 320 substantially opposite the tissue-side opening 315. The ambient-side opening 320 preferably corresponds to the dimensions of the extended portion 205 of the detector 125. Thus, as the detector 125 is inserted into the detector pocket 310, the extended portion 205 of the detector 125 protrudes through the ambient-side opening 320, thereby further seating and securing the optical probe 110.

Figure 3B:
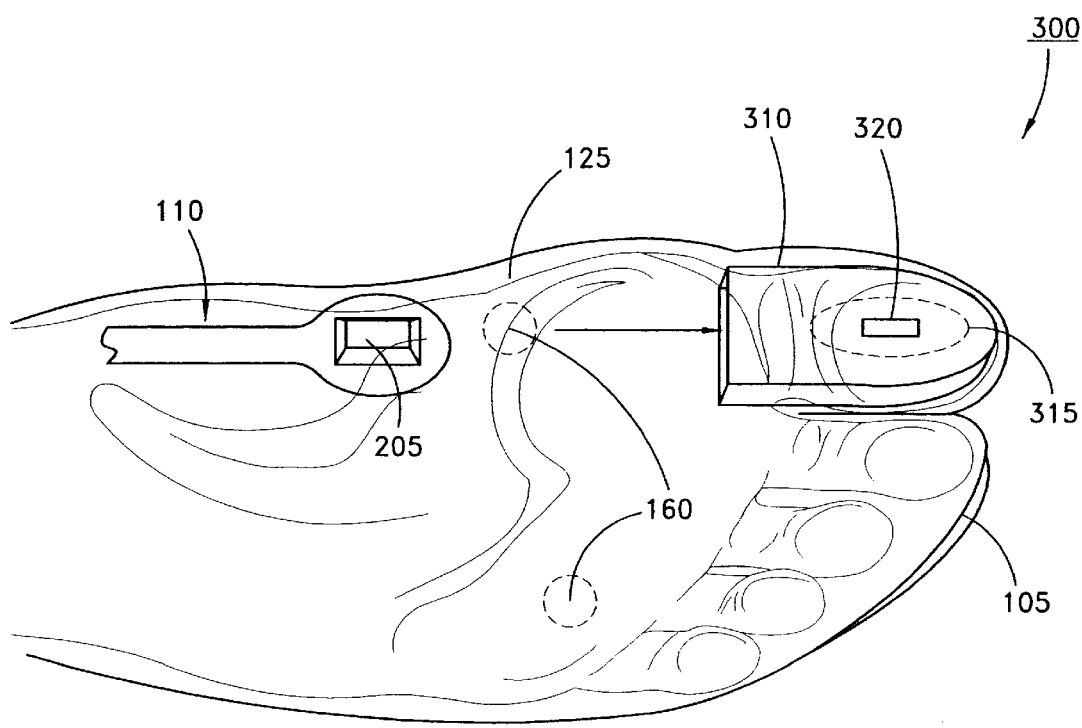
FIG. 3B illustrates a bottom view of the probe positioner of FIG. 3A.

FIG. 3B illustrates a bottom view of the probe positioner 300 of FIG. 3A. As shown in FIG. 3B, the detector pocket 310 aligns substantially parallel to, and beneath, the great toe. Moreover the detector pocket 310 preferably covers the tissue-side opening 315 in the sock 105. The detector pocket 310 includes the ambient-side opening 320. As mentioned in the foregoing, the extended portion 205 of the detector 125 preferably protrudes through the ambient-side opening 320. Thus, the detector pocket 310 preferably seats and secures the detector 125 to the measurement site.

A skilled artisan will understand from the disclosure herein that the pockets 305 and 310 may include a wide number of possible configurations. For example, the detector pocket 310 may be formed without the tissue-side or ambient-side openings, 315 and 320, respectively. In addition, the emitter pocket 305 may advantageously include the ambient-side opening 320.

According to this embodiment, a clinician may advantageously direct the optical probe 110 into the pockets 305 and 310, thereby securing the optical probe 110 in the disposable sock 105. The optical probe 110 then provides signals to the oximeter system. Thereafter, the optical probe 110 is removed from the disposable sock 105, and the disposable sock 105 is discarded. According to one embodiment, the optical probe 110 is sterilized and then reused in another disposable sock 105.

Although the foregoing has disclosed the pockets 305 and 310 in terms of preferred and alternative embodiments, a skilled artisan will recognize from the disclosure herein a wide number of configurations that provide a disposable sock to be fitted with a reusable optical probe.

Although the probe positioner 300 is disclosed according to the preferred and alternative embodiments of positioning the optical probe 110 over one of the wearer's toes, as mentioned in the foregoing, a skilled artisan will recognize from the disclosure herein other measurement sites that may advantageously be used. For example, FIG. 3B illustrates other measurement sites 160 for preferably positioning the detector 125 of the optical probe 110. As mentioned, such alternative sites 160 may be advantageous for patients having poor perfusion in the furthest extremities.

Figure 4:
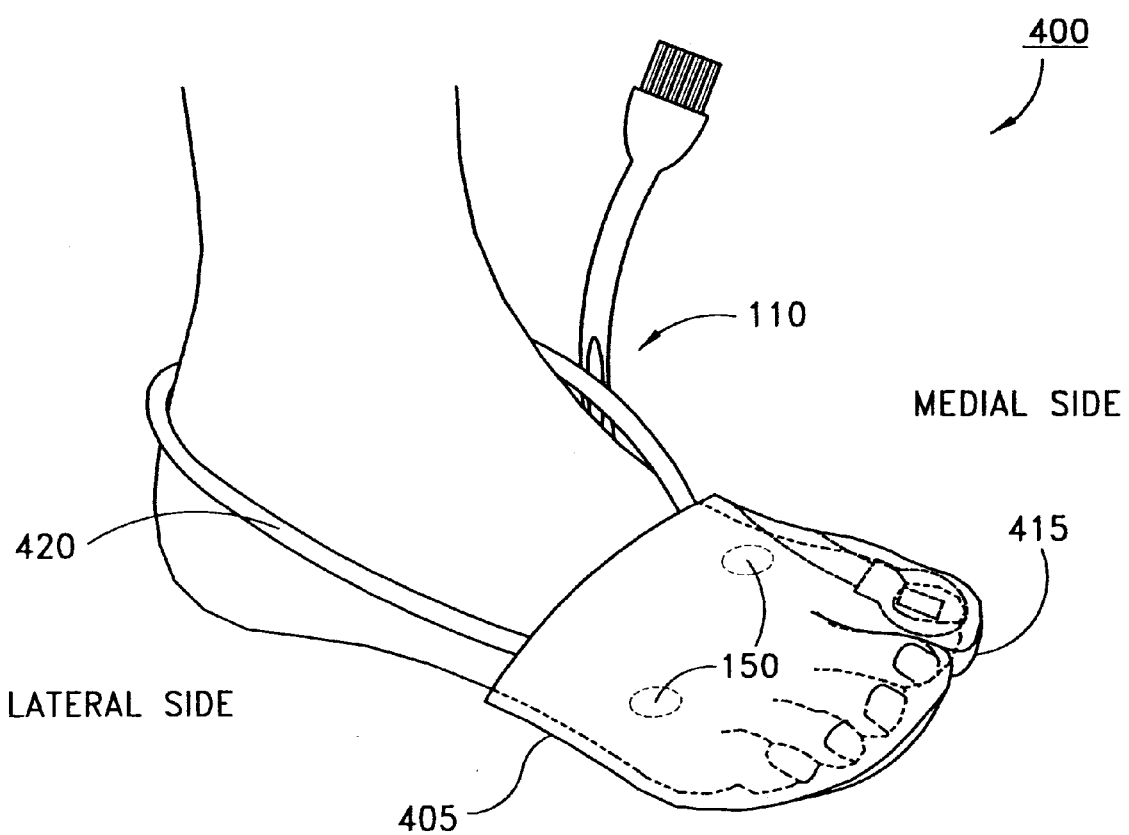
FIG. 4 illustrates a perspective view of a probe positioner having features according to yet another embodiment of the invention.

FIG. 4 illustrates a perspective view of a probe positioner 400 having features according to yet another embodiment of the invention. As shown in FIG. 4, the probe positioner 400 comprises a toecap 405 fitted with the optical probe 110 and having features similar to those of the foregoing sock 105. For example, the material of the toecap 405 preferably includes elastomeric material providing a friction form fit advantageously prepositioning the optical probe 110. The toecap 405 further includes a positioning portion 415 configured to receive the great toe of the wearer. As with the positioning portion 115 of FIG. 1, the positioning portion 415 of FIG. 4 prevents the rotation of the toecap 405 and provides added securement for the optical probe 110.

As shown in FIG. 4, the toecap 405 includes a strap 420 preferably securing the toecap 405 over the wearer's toes. The strap 420 preferably extends around the wearer's heel such that the strap does not easily fall off during agitation. The strap 420 preferably comprises an elastomeric material such that it can be stretched around the heel of the wearer. Thus, the toecap 405 and the strap 420 provide for efficient, single motion application of the optical probe 110 to the measurement site on the great toe. Moreover, the strap 420 provides that a given size of the probe positioner 400 may advantageously be workable for a wide number of actual foot sizes. Alternatively, the strap 420 may include a fastener so as to allow for adjustability in the length thereof. For example, the fastener may include a buckle, Velcro, snap, or the like.

According to an alternative embodiment, the strap 420 may advantageously include skin protection for protecting the tissue from the strap 420. The skin protection also advantageously increases the surface area of the strap 420, thereby mitigating focused pressure from long-term application that may cause sores or poor perfusion. According to one embodiment, the strap 420 may include a skin protector like those commercially sold under the name Softees.

Although the foregoing invention has been described in terms of certain preferred embodiments, other embodiments will be apparent to those of ordinary skill in the art from the disclosure herein. For example, a skilled artisan may advantageously recognize combinations of features from the various embodiments are combinable with other embodiments. For example, the toecap 405 may advantageously include multiple toe positioning portions for toes other than the great toe. Moreover, the toecap 405 may comprise tubular stretch net material.

Figure 5:
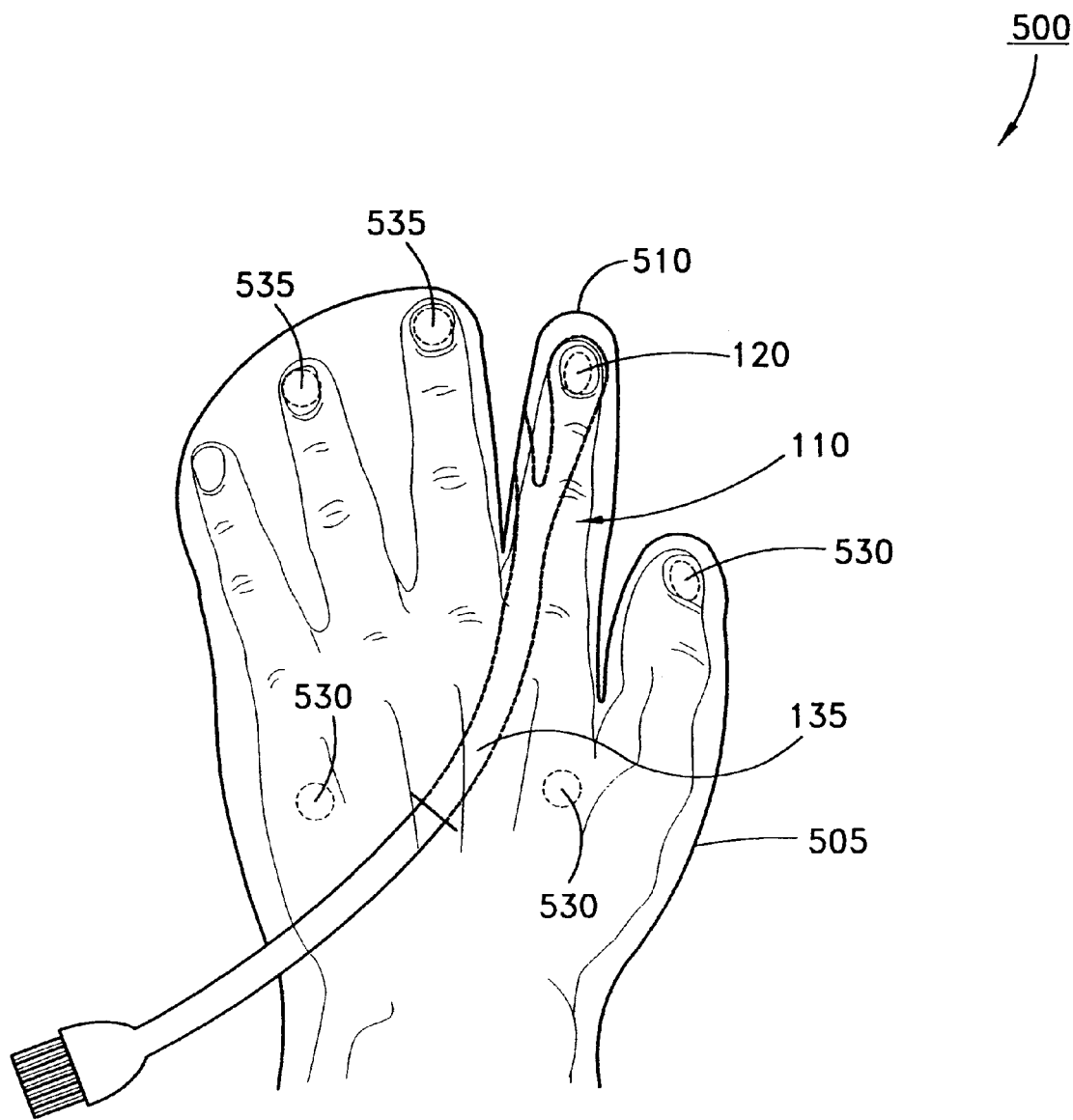
FIG. 5 illustrates a perspective view of a probe positioner having features according to an embodiment of the invention.

FIG. 5 illustrates a perspective view of a probe positioner 500 having features according to yet another embodiment of the invention. As shown in FIG. 5, the probe positioner 500 includes a sock 505 fitted with the optical probe 110. The sock 505 is configured to receive the hand of the wearer so as to position and substantially secure the emitter 120 of the optical probe 110 over a measurement site. Similar to the foregoing sock 105 or toecap 405, the sock 505 preferably comprises an elastomeric or stretchable material. The elastomeric material preferably stretches during application of the sock 505 to the wearer's hand, and shrinks thereafter, such that the sock 505 substantially forms to the shape of the wearer's hand. Preferably, the sock 505 is configured for various hand sizes such that the elasticity of the material applies only a small amount of pressure to the tissue of the measurement site. Thus, the preferred embodiment of the sock 505 provides a securing mechanism that substantially forms to the shape of the wearer's hand, thereby providing positioning rigidity over a wide surface area. Accordingly, the sock 105 advantageously avoids the application of pressure sufficient to cause poor circulation and/or sores on a small surface area. According to an alternative embodiment, the sock 505 advantageously comprises the foregoing tubular stretch net material.

FIG. 5 also illustrates the sock 505 including a positioning portion 510. The positioning portion 510 preferably comprises a pocket-like structure similar to that of the finger of a glove such that the positioning portion 510 separately receives at least one of the three middle fingers of the wearer's hand. The positioning portion 510 advantageously prevents rotation of the sock 505 around the wearer's hand, thereby advantageously providing additional securement for the optical probe 110. According to the embodiment shown in FIG. 5, the positioning portion 510 preferably covers the finger adjacent the wearer's thumb. However, alternative embodiments may advantageously include another one or a combination of any of the wearer's middle three fingers.

Although the probe positioner 500 is disclosed according to the preferred and alternative embodiments of positioning the optical probe 110 over one of the wearer's fingers, a skilled artisan will recognize from the disclosure herein other measurement sites that may advantageously be used. For example, FIG. 5 illustrates other measurement sites 535 for preferably positioning the emitter 120 of the optical probe 110. Such alternative sites 535 may be advantageous for patients having poor perfusion in one or more of the other three middle fingers. In addition, FIG. 5 illustrates yet other measurement sites 530 for preferably positioning the emitter 120 of the optical probe 110. The sites 530 are preferable for use with infants whose fingers may be too small for the optical probe 110 to function reliably. Moreover, a skilled artisan may recognize additional sites from the disclosure herein for advantageously positioning the optical probe 110 using the socks 105 and 505, or the toecap 405. For example, the smallest, or pinky finger may be used.

In addition to the preferred and alternate embodiments of the probe positioner 500, a skilled artisan will recognize that the probe positioner 500 may advantageously include any, some, or all of the features and aspects discussed in the foregoing description of FIGS. 1–4. For example, the probe positioner 500 may advantageously include a timer circuit or a fingercap. In addition, the sock 505 may advantageously be disposable or may advantageously be disposable and incorporate reusable circuitry.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site, wherein the positioning portion is configured to receive a great toe of the wearer.

2. The optical probe positioner of claim 1, wherein the at least one portion receiving more than one digit of the wearer receives one or more other toes.

3. The optical probe positioner of claim 1, wherein the optical probe comprises a pulse oximeter probe.

4. The optical probe positioner of claim 1, wherein the optical probe comprises a Y-shaped section, wherein one branch of the Y-shaped section connects to an emitter, another branch of the Y-shaped section connects to a detector, and another branch of the Y-shaped section connects to an oximeter system.

5. The optical probe positioner of claim 1, wherein the optical probe comprises reusable circuitry.

6. The optical probe positioner of claim 5, wherein the sock comprises pockets for substantially securing the reusable circuitry at the measurement site.

7. The optical probe positioner of claim 1, further comprising a timer circuit.

8. The optical probe positioner of claim 7, wherein the timer circuit includes an alarm.

9. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site, wherein the positioning portion is configured to receive one or more of three middle fingers of a hand of the wearer.

10. The optical probe positioner of claim 9, wherein the at least one portion receiving more than one digit of the wearer receives one or more other fingers or a thumb.

11. The optical probe positioner of claim 9, wherein the optical probe comprises a pulse oximeter probe.

12. The optical probe positioner of claim 9, wherein the optical probe comprises a Y-shaped section, wherein one branch of the Y-shaped section connects to an emitter, another branch of the Y-shaped section connects to a detector, and another branch of the Y-shaped section connects to an oximeter system.

13. The optical probe positioner of claim 9, wherein the optical probe comprises reusable circuitry.

14. The optical probe positioner of claim 13, wherein the sock comprises pockets for substantially securing the reusable circuitry at the measurement site.

15. The optical probe positioner of claim 9, further comprising a timer circuit.

16. The optical probe positioner of claim 15, wherein the timer circuit includes an alarm.

17. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site, wherein the sock comprises an elastomeric material such that the sock substantially conforms to the wearer's hand thereby forming a friction fit over a large surface area.

18. The optical probe positioner of claim 17, wherein a portion of the optical probe is embedded in the sock.

19. The optical probe positioner of claim 17, wherein the optical probe comprises an emitter and a detector and wherein the sock comprises an opening such that the emitter and the detector contact the tissue at the measurement site.

20. The optical probe positioner of claim 17, wherein the optical probe comprises a detector having an extended portion, and wherein the sock comprises an opening such that the extended portion protrudes from the sock through the opening, the sock thereby forming a more secure friction fit around the detector near the opening.

21. The optical probe positioner of claim 17, wherein the optical probe comprises a pulse oximeter probe.

22. The optical probe positioner of claim 17, wherein the optical probe comprises a Y-shaped section, wherein one branch of the Y-shaped section connects to an emitter, another branch of the Y-shaped section connects to a detector, and another branch of the Y-shaped section connects to an oximeter system.

23. The optical probe positioner of claim 17, wherein the optical probe comprises reusable circuitry.

24. The optical probe positioner of claim 23, wherein the sock comprises pockets for substantially securing the reusable circuitry at the measurement site.

25. The optical probe positioner of claim 17, further comprising a timer circuit.

26. The optical probe positioner of claim 25, wherein the timer circuit includes an alarm.

27. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site, wherein the positioning portion is configured to receive at least a thumb of a hand of the wearer.

28. The optical probe positioner of claim 27, wherein the sock comprises a tubular stretch net material.

29. The optical probe positioner of claim 27, wherein the optical probe comprises a pulse oximeter probe.

30. The optical probe positioner of claim 27, wherein the optical probe comprises a Y-shaped section, wherein one branch of the Y-shaped section connects to an emitter, another branch of the Y-shaped section connects to a detector, and another branch of the Y-shaped section connects to an oximeter system.

31. The optical probe positioner of claim 27, wherein the optical probe comprises reusable circuitry.

32. The optical probe positioner of claim 31, wherein the sock comprises pockets for substantially securing the reusable circuitry at the measurement site.

33. The optical probe positioner of claim 27, further comprising a timer circuit.

34. The optical probe positioner of claim 33, wherein the timer circuit includes an alarm.

35. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site, wherein the sock comprises a toecap.

36. The optical probe positioner of claim 35, wherein the toecap includes a strap securing the toecap over the toes of the wearer.

37. The optical probe positioner of claim 36, wherein the positioning portion is configured to receive a great toe of the wearer.

38. The optical probe positioner of claim 35, wherein the optical probe comprises a pulse oximeter probe.

39. The optical probe positioner of claim 35, wherein the optical probe comprises a Y-shaped section, wherein one branch of the Y-shaped section connects to an emitter, another branch of the Y-shaped section connects to a detector, and another branch of the Y-shaped section connects to an oximeter system.

40. The optical probe positioner of claim 35, wherein the optical probe comprises reusable circuitry.

41. The optical probe positioner of claim 40, wherein the sock comprises pockets for substantially securing the reusable circuitry at the measurement site.

42. The optical probe positioner of claim 35, further comprising a timer circuit.

43. The optical probe positioner of claim 42, wherein the timer circuit includes an alarm.

44. An optical probe positioner comprising a sock fitted with an optical probe, configured to be applied to a measurement site, and including at least one positioning portion substantially preventing the sock from rotating around the measurement site, and at least one portion receiving more than one digit of a wearer, wherein the optical probe measures at least one characteristic of tissue at the measurement site wherein the sock comprises one of a glove and a mitten.

45. The optical probe positioner of claim 44, wherein the optical probe comprises a pulse oximeter probe.

46. The optical probe positioner of claim 44, wherein the optical probe comprises a Y-shaped section, wherein one branch of the Y-shaped section connects to an emitter, another branch of the Y-shaped section connects to a detector, and another branch of the Y-shaped section connects to an oximeter system.

47. The optical probe positioner of claim 44, wherein the optical probe comprises reusable circuitry.

48. The optical probe positioner of claim 47, wherein the sock comprises pockets for substantially securing the reusable circuitry at the measurement site.

49. The optical probe positioner of claim 44, further comprising a timer circuit.

50. The optical probe positioner of claim 49, wherein the timer circuit includes an alarm.

51. A sock substantially conforming to a wearer's foot and configured to apply an optical probe to a measurement site, the sock comprising:

a form fitting material which substantially conforms to a wearer's foot and which is fitted with sensor elements of an optical probe; and at least one positioning portion within the form fitting material preventing the form fitting material from rotating around a measurement site, wherein the optical probe measures at least one characteristic of tissue at the measurement site.

52. The sock of claim 51, wherein the positioning portion is configured to receive a great toe of the wearer.

53. The sock of claim 51, further comprising at least one additional positioning portion configured to receive more than one toe.

54. The sock of claim 51, wherein the form fitting material comprises an elastomeric material forming a friction fit over a large surface area.

55. The sock of claim 51, wherein the optical probe comprises a pulse oximeter probe.

56. The sock of claim 51, wherein the sock comprises a toecap.

57. The sock of claim 56, wherein the toecap includes a strap securing the toecap over the toes of the wearer.

58. The sock of claim 51, further comprising a flex circuit that connects to the optical probe.

59. The sock of claim 51, further comprising a timer circuit.

\* \* \* \* \*